(12) United States Patent
Kitamura et al.

(10) Patent No.: US 9,745,410 B2
(45) Date of Patent: Aug. 29, 2017

(54) AROMATIC ALDEHYDE, AND EPOXY RESIN CURING AGENT AND EPOXY RESIN COMPOSITION COMPRISING THE AROMATIC ALDEHYDE

(71) Applicant: Mitsubishi Gas Chemical Company, Inc., Chiyoda-ku (JP)

(72) Inventors: Mitsuharu Kitamura, Okayama (JP); Yutaka Matsuura, Okayama (JP); Hisayuki Kuwahara, Kanagawa (JP); Tomotaka Wada, Kanagawa (JP); Yuiga Asai, Kanagawa (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 320 days.

(21) Appl. No.: 14/404,560

(22) PCT Filed: May 17, 2013

(86) PCT No.: PCT/JP2013/063786
§ 371 (c)(1),
(2) Date: Nov. 28, 2014

(87) PCT Pub. No.: WO2013/179915
PCT Pub. Date: Dec. 5, 2013

(65) Prior Publication Data
US 2015/0111991 A1    Apr. 23, 2015

(30) Foreign Application Priority Data
May 29, 2012    (JP) .................... 2012-121735

(51) Int. Cl.
*C08G 59/56*    (2006.01)
*C08G 59/40*    (2006.01)
(Continued)

(52) U.S. Cl.
CPC ............. *C08G 59/56* (2013.01); *B01J 27/12* (2013.01); *C07C 45/49* (2013.01); *C07C 45/50* (2013.01);
(Continued)

(58) Field of Classification Search
CPC ............... C08G 59/56; C08G 59/4007; C08G 59/4223; C08G 59/58; C07C 45/50;
(Continued)

(56) References Cited

U.S. PATENT DOCUMENTS 3,244,668 A * 4/1966 Knapp .................. C08K 5/315
106/169.41
4,122,191 A * 10/1978 Parker .................... C07C 45/41
514/688
(Continued)

FOREIGN PATENT DOCUMENTS

JP    58 109567    6/1983
JP    4 46179    2/1992
(Continued)

OTHER PUBLICATIONS

International Preliminary Report on Patentability and Written Opinion issued on Dec. 2, 2014 in PCT/JP2013/063786 filed May 17, 2013.
(Continued)

*Primary Examiner* — Randy Gulakowski
*Assistant Examiner* — Ha S Nguyen
(74) *Attorney, Agent, or Firm* — Oblon, McClelland, Maier & Neustadt, L.L.P.

(57) ABSTRACT

There are provided a novel aromatic aldehyde compound capable of providing an epoxy resin coating film and an epoxy resin cured material satisfying all of the excellent surface property (smoothness, gloss), drying property, water resistance, transparency and adhesion, and an epoxy resin curing agent and an epoxy resin composition containing the aromatic aldehyde compound. The aromatic aldehyde has a branched alkyl group having 10 to 14 carbon atoms.

8 Claims, 12 Drawing Sheets

(51) Int. Cl.
*C07C 45/50* (2006.01)
*C07C 47/228* (2006.01)
*C07C 45/49* (2006.01)
*C07C 47/542* (2006.01)
*C09D 163/00* (2006.01)
*C08G 59/58* (2006.01)
*C08G 59/42* (2006.01)
*B01J 27/12* (2006.01)

(52) U.S. Cl.
CPC .......... *C07C 47/228* (2013.01); *C07C 47/542* (2013.01); *C08G 59/4007* (2013.01); *C09D 163/00* (2013.01); *C08G 59/4223* (2013.01); *C08G 59/58* (2013.01)

(58) Field of Classification Search
CPC ..... C07C 47/228; C07C 45/49; C07C 47/542; B01J 27/12; C09D 163/00
See application file for complete search history.

(56) References Cited

U.S. PATENT DOCUMENTS

| 5,371,284 A | 12/1994 | Friary et al. | |
|---|---|---|---|
| 2004/0077800 A1* | 4/2004 | Umeyama | C08G 59/621 |
| | | | 525/523 |
| 2005/0085670 A1* | 4/2005 | Kato | C07C 45/49 |
| | | | 568/428 |

FOREIGN PATENT DOCUMENTS

| JP | 7 48430 | 2/1995 |
| JP | 7 258364 | 10/1995 |
| JP | 9 176614 | 7/1997 |
| JP | 2000 212255 | 8/2000 |
| JP | 2000-290351 | 10/2000 |
| JP | 2005-532255 A | 10/2005 |
| JP | 2008-116677 A | 5/2008 |
| WO | WO 03/008367 A2 | 1/2003 |

OTHER PUBLICATIONS

"General Introduction to Epoxy Resins, Basic Edition I", The Japan Society of Epoxy Resin Technology, pp. 119-122 and 132-135, (Nov. 19, 2003).
Osman, M., "Synthesis of Unbranched 4-Alkylbenzaldehydes", Helvetica Chimica Acta, vol. 65, Issue 8, No. 241, pp. 2448-2449, (1982).
Shinya, S., "Journal of Agricultural Chemical Society of Japan", vol. 33, No. 5, pp. 362-365, (1959).
International Search Report Issued Jul. 30, 2013 in PCT/JP13/063786 Filed May 17, 2013.
Xavier Garcias, et al, Palladium Catalyzed Synthesis of Chromenes and Chromenols, Tetrahedron Letters, vol. 32, No. 52, 1991, pp. 7739-7742.

* cited by examiner

[FIG. 1]
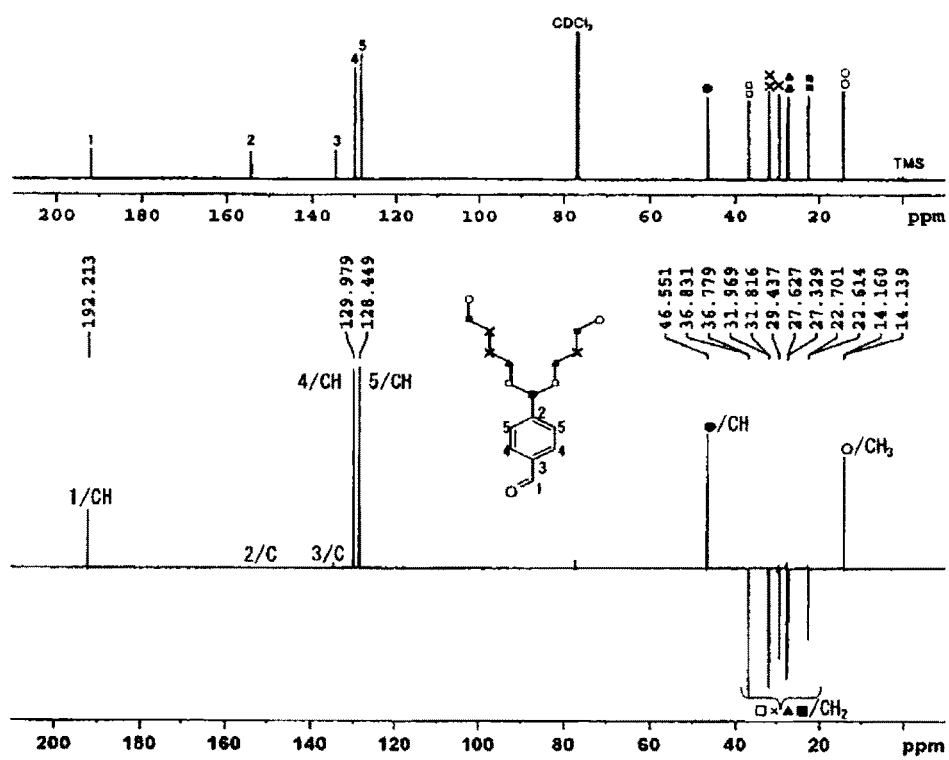

[FIG. 2]
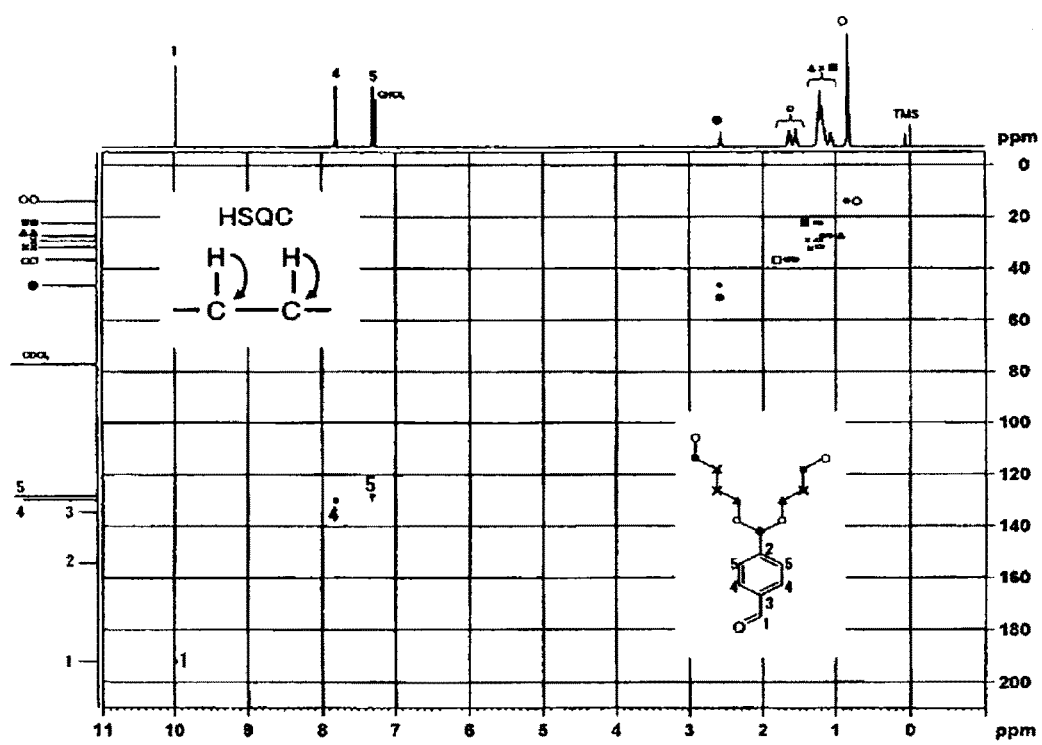

[FIG. 3]
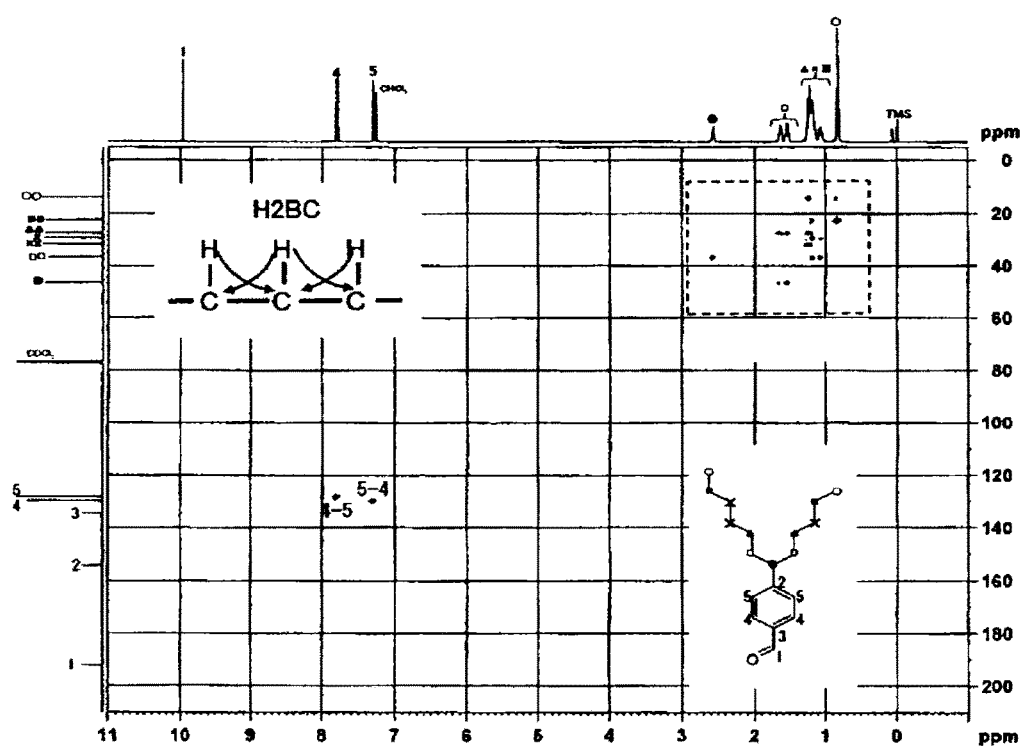

[FIG. 4]
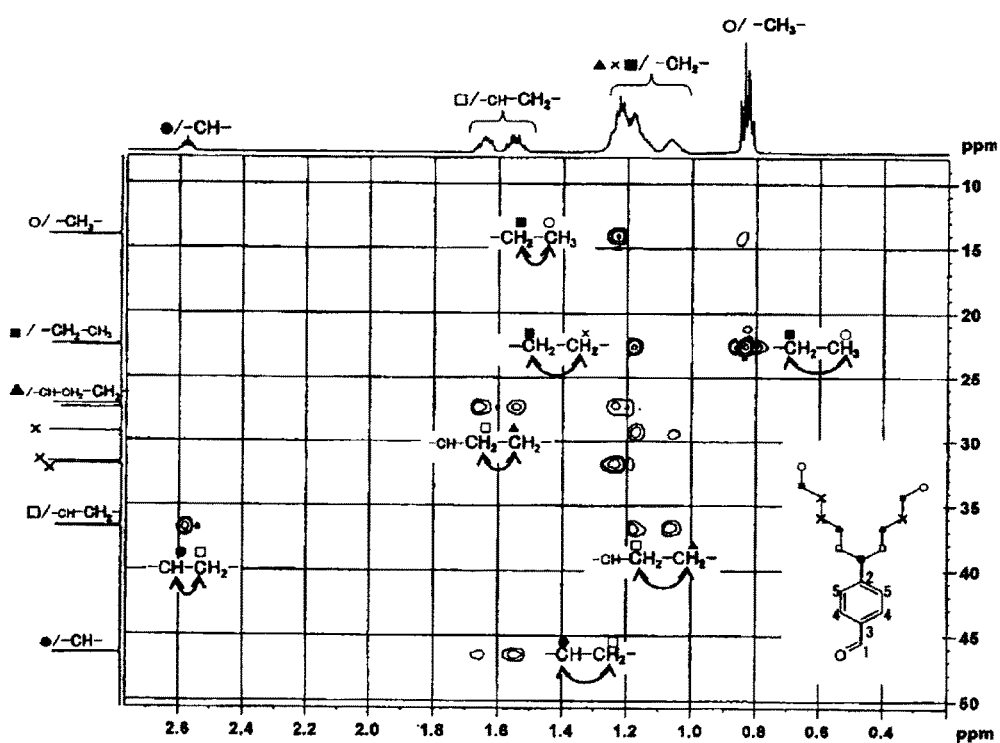

[FIG. 5]
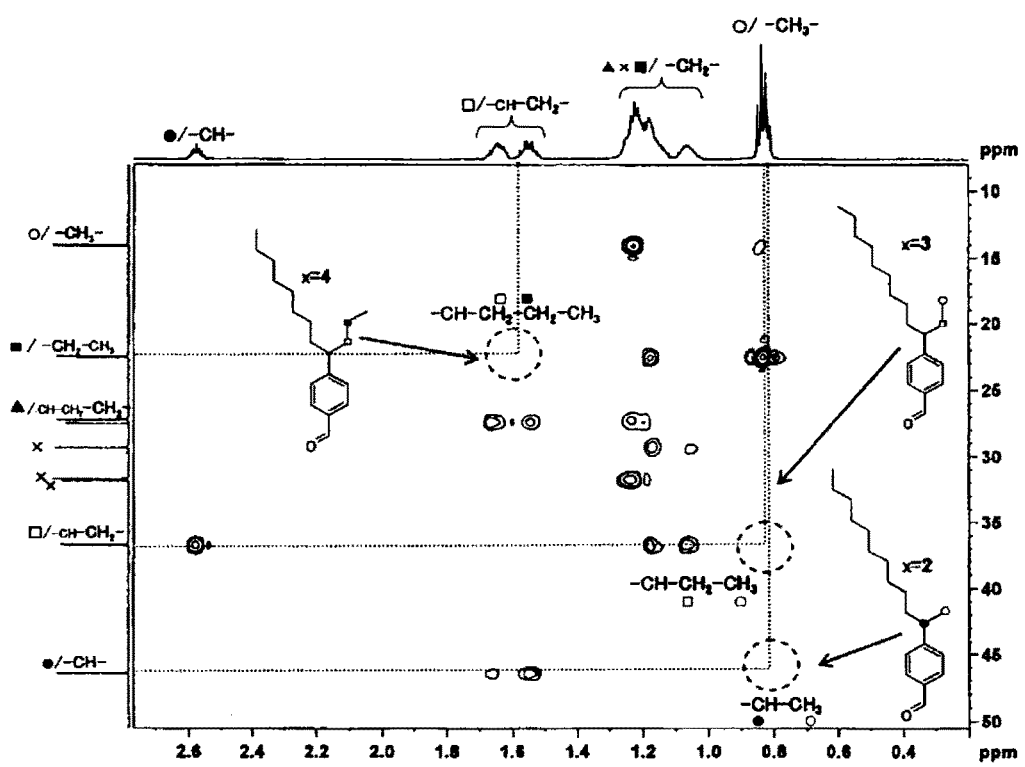

[FIG. 6]
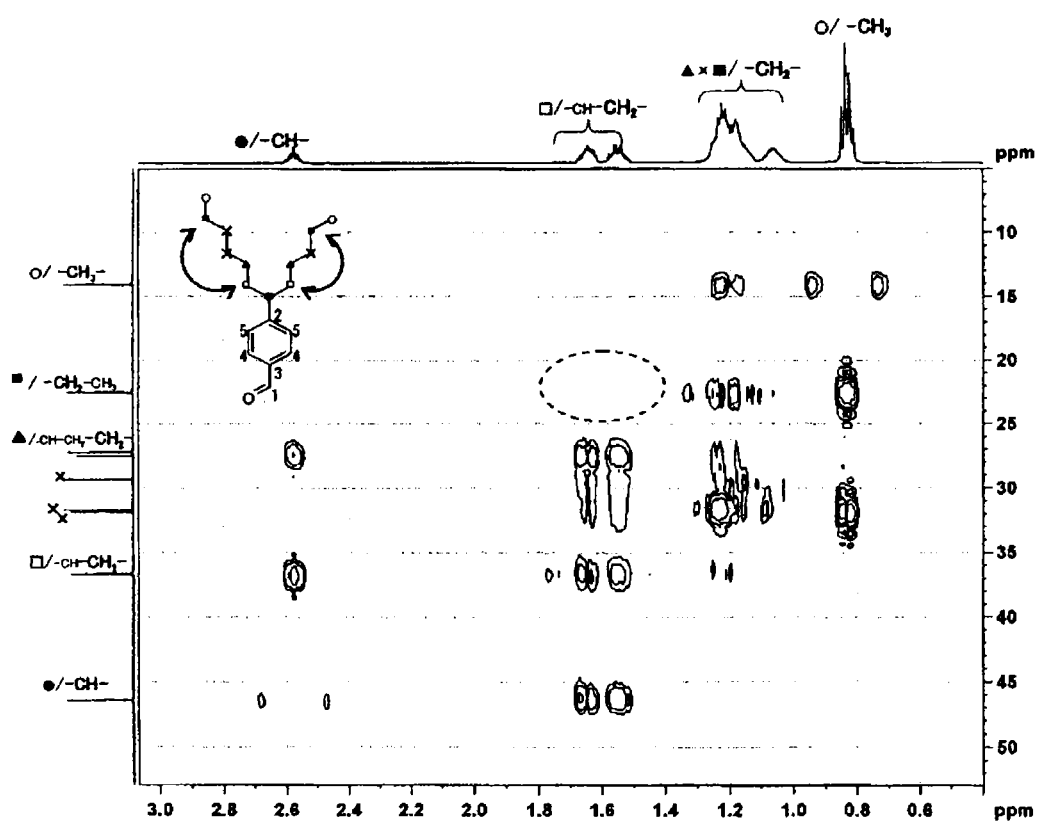

[FIG. 7]
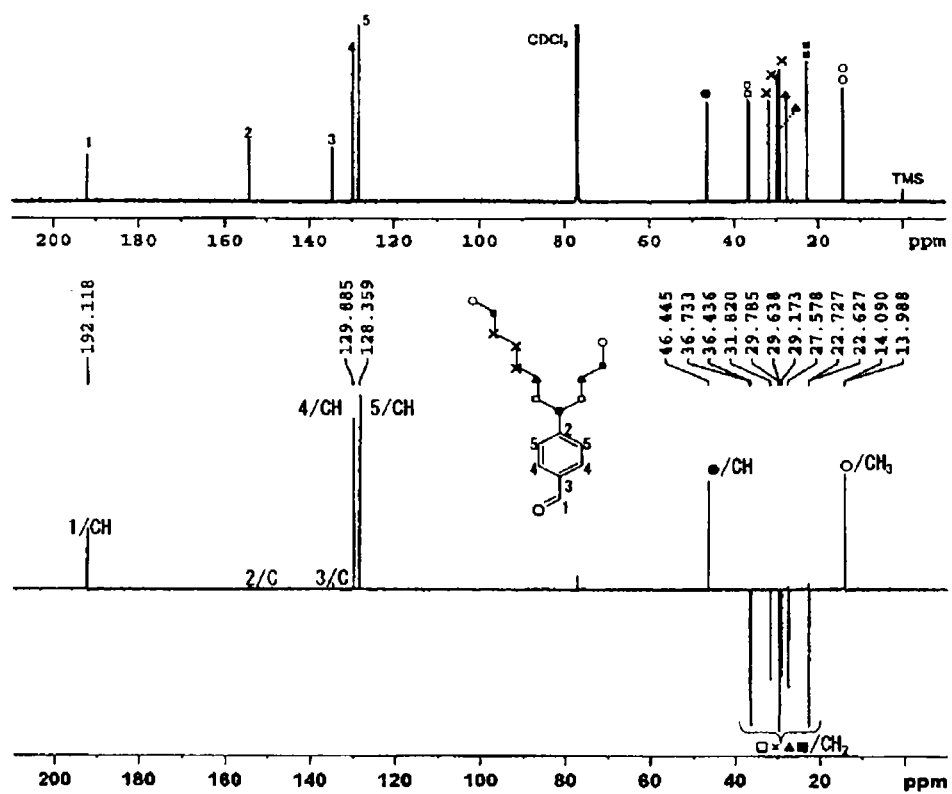

[FIG. 8]
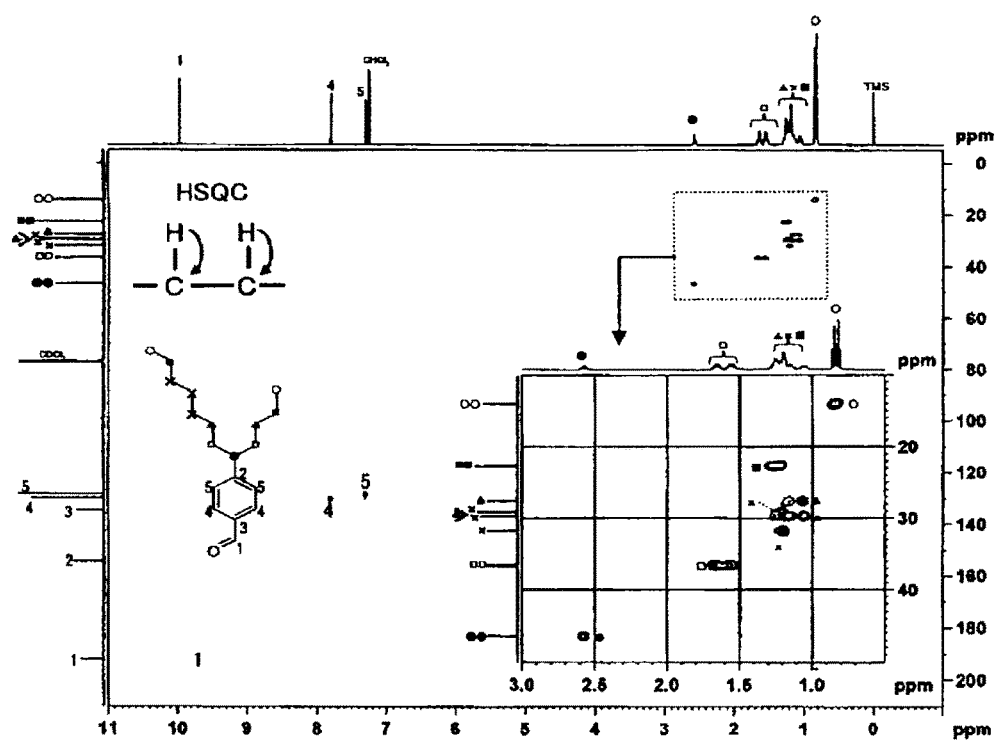

[FIG. 9]
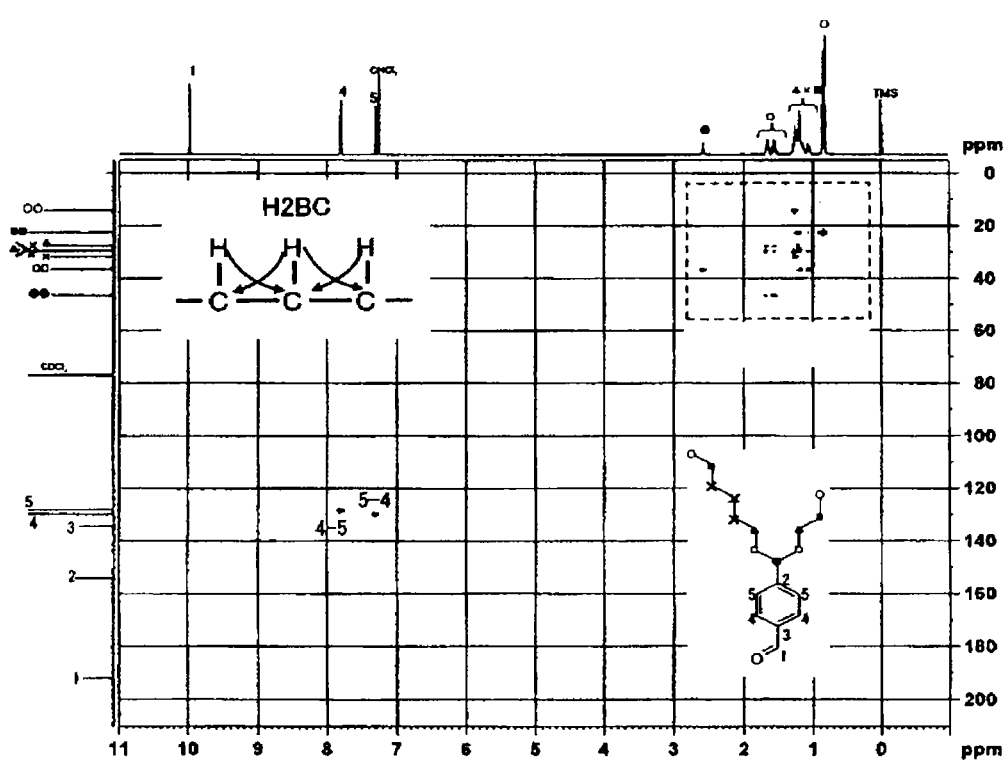

[FIG. 10]
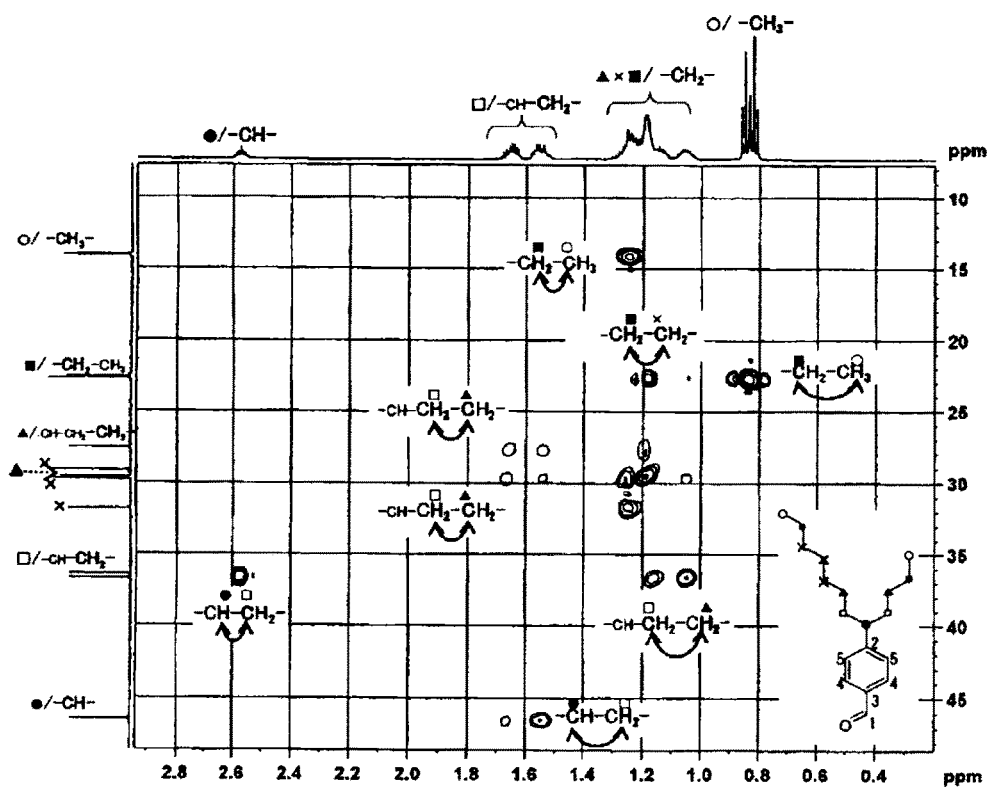

[FIG. 11]
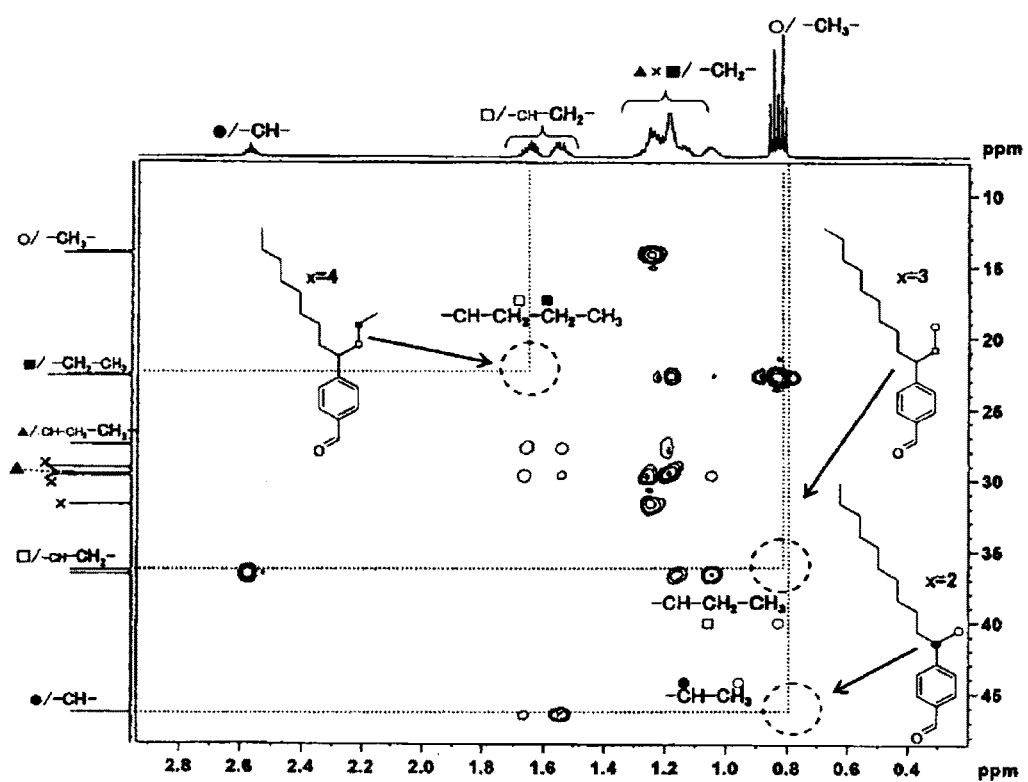

[FIG. 12]
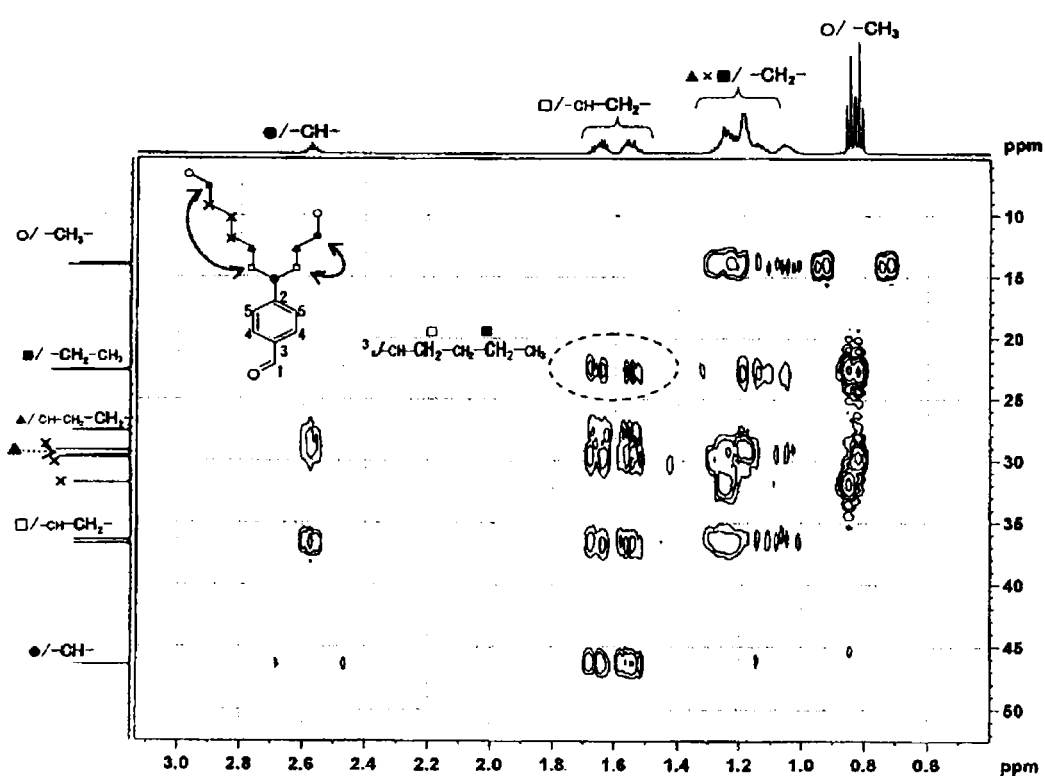

AROMATIC ALDEHYDE, AND EPOXY RESIN CURING AGENT AND EPOXY RESIN COMPOSITION COMPRISING THE AROMATIC ALDEHYDE

TECHNICAL FIELD

The present invention relates to an aromatic aldehyde, particularly to an aromatic aldehyde useful as a raw material for producing various types of industrial chemical raw materials, pharmaceuticals, agrochemicals, optical functional materials and electronic functional materials. The present invention further relates to an epoxy resin curing agent comprising the aromatic aldehyde, and an epoxy resin composition comprising the epoxy resin curing agent, particularly to an epoxy resin curing agent suitable for coating applications and civil engineering and construction applications, and an epoxy resin composition comprising the epoxy resin curing agent.

BACKGROUND ART

Various types of polyamine compounds are well known to be broadly used as epoxy resin curing agents and raw materials thereof (for example, see Patent Literature 1). Epoxy resin compositions utilizing these epoxy resin curing agents are broadly utilized in the coating fields such as anticorrosive coatings for marine vessels, bridges, and iron structures on land or the sea, and in the civil engineering and construction fields such as linings, reinforcements and repairing of concrete structures, floor materials of buildings, linings of water supply and sewage, pavement materials, and adhesive agents.

Epoxy resin curing agents using as a raw material a linear aliphatic polyamine such as diethylenetriamine and triethylenetetramine, or xylylenediamine among various types of polyamine compounds can impart better curability to epoxy resin compositions and also can impart good performance and physical properties to epoxy resin cured coating films and epoxy resin cured materials, than epoxy resin curing agents using as a raw material other polyamine compounds (for example, see Non Patent Literature 1).

CITATION LIST

Patent Literature

Patent Literature 1: Japanese Patent Laid-Open No. 58-109567

Non Patent Literature

Non Patent Literature 1: "General Introduction to Epoxy Resins, Basic Edition I", edited and published by The Japan Society of Epoxy Resin Technology, 2003 (in Japanese)

SUMMARY OF INVENTION

Technical Problem

However, epoxy resin compositions comprising an epoxy resin curing agent using xylylenediamine as a raw material are liable to absorb carbon dioxide and water vapor in the air to form a carbamate salt and a carbonate salt. The formation of a carbamate salt or a carbonate salt poses problems of bringing about the reduction of the performance, the deterioration of the surface property (smoothness, gloss) and the reduction of the drying property of epoxy resin cured coating films, and the reduction of the physical properties and the adhesion of epoxy resin cured materials, and the problem of causing whitening due to the reduction of water resistance and deteriorating the appearance.

In order to improve the surface property, the drying property and the water resistance of epoxy resin coating films and epoxy resin cured materials, various types of additives are used. However, some additives pose the following problems: the improvement of the water resistance is insufficient though the surface property and the drying property can be improved; the improvement of the surface property and the drying property is insufficient though the water resistance can be improved; and, the transparency is reduced and the adhesion of an epoxy resin coating film to a base material is reduced though the surface property, the drying property and the water resistance can be improved.

In consideration of the above situation, the technical problem of the present invention is to provide a novel aromatic aldehyde compound capable of providing an epoxy resin coating film and an epoxy resin cured material satisfying all of the excellent surface property (smoothness, gloss), drying property, water resistance, transparency and adhesion, and an epoxy resin curing agent and an epoxy resin composition comprising the aromatic aldehyde compound.

Solution to Problem

As a result of exhaustive studies to solve the above problem, the present inventors have found that the use of an epoxy resin composition comprising an epoxy resin curing agent comprising a polyamine compound and an aromatic aldehyde having a specific structure enables to provide an epoxy resin coating film and an epoxy resin cured material satisfying all of the excellent surface property, drying property, water resistance, transparency and adhesion.

That is, the present invention is as follows.

[1]
An aromatic aldehyde having a branched alkyl group, wherein the branched alkyl group has 10 to 14 carbon atoms.

[2]
The aromatic aldehyde according to the above [1], being represented by the following general formula (II):

[Formula 1]

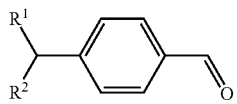

(II)

(wherein $R^1$ and $R^2$ each independently represent an alkyl group having 1 to 12 carbon atoms, and a total number of the carbon atoms of $R^1$ and $R^2$ is 9 to 13.)

[3]
The aromatic aldehyde according to the above [1] or [2], being one or more selected from the group consisting of 4-(dodecan-6-yl)benzaldehyde and 4-(dodecan-5-yl)benzaldehyde.

[4]
An epoxy resin curing agent, comprising (A) a polyamine compound and (B) an aromatic aldehyde according to any of the above [1] to [3].

[5]

The epoxy resin curing agent according to the above [4], wherein (A) the polyamine compound is one or more selected from the group consisting of polyamines represented by the following general formula (A1), linear aliphatic polyamines represented by the following general formula (A2) and compounds obtained by adding a polyamine represented by the following general formula (A1) or (A2) to a compound having at least one glycidyl group in one molecule thereof:

$$H_2N-CH_2-A-CH_2-NH_2 \quad (A1)$$

wherein A represents a phenylene group or a cyclohexylene group; and $$H_2N-(CH_2CH_2NH)_n-CH_2CH_2NH_2 \quad (A2)$$

wherein n represents an integer of 0 to 4.

[6]

An epoxy resin composition, comprising an epoxy resin curing agent according to the above [4] or [5].

[7]

The epoxy resin composition according to the above [6], used for coating or for civil engineering and construction.

An epoxy resin cured coating film, being obtained by curing the epoxy resin composition for coating according to the above [7].

[9]

An epoxy resin cured material, being obtained by curing the epoxy resin composition for civil engineering and construction according to the above [7].

[10]

A method for producing an aromatic aldehyde according to any of the above [1] to [3], the method comprising a step of formylating an aromatic compound which has a branched alkyl group having 10 to 14 carbon atoms with carbon monoxide in a presence of hydrogen fluoride and boron trifluoride.

Advantageous Effects of Invention

The epoxy resin composition comprising an epoxy resin curing agent comprising the aromatic aldehyde according to the present invention can provide an epoxy resin coating film and an epoxy resin cured material satisfying all of the excellent surface property (smoothness, gloss), drying property, water resistance, transparency and adhesion.

BRIEF DESCRIPTION OF DRAWINGS

FIG. 1 shows a result of a dept135-NMR measurement on Component 1 (4-(dodecan-6-yl)benzaldehyde) in Example 1.

FIG. 2 shows a result of an HSQC-NMR measurement on Component 1 in Example 1.

FIG. 3 shows a result of an H2BC-NMR measurement on Component 1 in Example 1.

FIG. 4 is an enlarged view of the part from 0.2 to 2.7 ppm (the part relevant to an alkyl group) of the measurement result part in FIG. 3.

FIG. 5 shows a result of a study on isomer candidate compounds by using the measurement result of FIG. 4.

FIG. 6 shows a result of an HMBC-NMR measurement on Component 1 in Example 1.

FIG. 7 shows a result of a dept135-NMR measurement on Component 2 (4-(dodecan-5-yl)benzaldehyde) in Example 1.

FIG. 8 shows a result of an HSQC-NMR measurement on Component 2 in Example 1.

FIG. 9 shows a result of an H2BC-NMR measurement on Component 2 in Example 1.

FIG. 10 is an enlarged view of the part from 0.2 to 2.9 ppm (the part relevant to an alkyl group) of the measurement result in FIG. 9.

FIG. 11 shows a result of a study on isomer candidate compounds by using the measurement result of FIG. 10.

FIG. 12 shows a result of an HMBC-NMR measurement on Component 2 in Example 1.

DESCRIPTION OF EMBODIMENTS

Hereinafter, an embodiment to practice the present invention (hereinafter, simply referred to as "the present embodiment") will be described in detail. The following present embodiment is only an exemplification to describe the present invention, and has no purport of limiting the present invention to the following. The present invention may be practiced with a suitable change or modification within the gist.

[Aromatic Aldehyde]

An aromatic aldehyde in the present embodiment is an aromatic aldehyde which has a branched alkyl group having 10 to 14 carbon atoms. From the viewpoint of providing an epoxy resin coating film satisfying all of the excellent surface property, drying property, water resistance, transparency and adhesion when being used for an epoxy resin curing agent, the aromatic aldehyde is preferably a p-alkylbenzaldehyde represented by the following general formula (I), and more preferably a p-alkylbenzaldehyde represented by the following general formula (II):

[Formula 2]

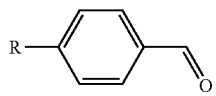

(I)

(wherein R represents a branched alkyl group having 10 to 14 carbon atoms.)

[Formula 3]

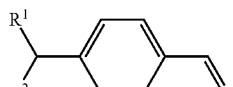

(II)

(In the formula, $R^1$ and $R^2$ each independently represent an alkyl group having 1 to 12 carbon atoms, and the total number of the carbon atoms of $R^1$ and $R^2$ is 9 to 13.)

The branched alkyl group represented by R in the general formula (I) may be branched at any site thereof. From the viewpoint of providing an epoxy resin coating film satisfying all of the excellent surface property, drying property, water resistance, transparency and adhesion when being used for an epoxy resin curing agent, R is preferably a branched alkyl group having 10 to 13 carbon atoms, and more preferably a dodecan-6-yl group or a dodecan-5-yl group.

Although the total number of the carbon atoms of $R^1$ and $R^2$ in the general formula (II) is required to be such a large number that the compound has a boiling point exceeding 330° C. at normal pressure from the viewpoint of the discharge regulation of volatile organic compounds (VOC), obtaining the product by distillation becomes difficult when the total number of the carbon atoms of $R^1$ and $R^2$ is too large. Therefore, the total number of the carbon atoms of $R^1$ and $R^2$ is preferably 9 to 13. The combination of $R^1$ and $R^2$ in the general formula (II) is preferably a combination of a n-butyl group and a n-heptyl group, or a combination of a n-pentyl group and a n-hexyl group.

Preferable specific examples of the aromatic aldehyde in the present embodiment include one or more selected from the group consisting of 4-(dodecan-6-yl)benzaldehyde and 4-(dodecan-5-yl)benzaldehyde.

The aromatic aldehyde in the present embodiment may be a mixture of two or more aromatic aldehydes which has a branched alkyl group having 10 to 14 carbon atoms, and is preferably a mixture of two or more aromatic aldehydes which has a branched alkyl group having 10 to 13 carbon atoms.

In the case where the aromatic aldehyde is a mixture of two or more aromatic aldehydes having a branched alkyl group having 10 to 13 carbon atoms, the composition ratio is preferably as follows: an aromatic aldehyde having a branched alkyl group having 10 carbon atoms is 10 to 15% by mass; an aromatic aldehyde having a branched alkyl group having 11 carbon atoms is 20 to 30% by mass; an aromatic aldehyde having a branched alkyl group having 12 carbon atoms is 25 to 35% by mass; and an aromatic aldehyde having a branched alkyl group having 13 carbon atoms is 20 to 30% by mass. If the composition ratio of an aromatic aldehyde mixture is in the above range, the melting point decreases and the workability of the mixture in the case of using the mixture for an epoxy resin curing agent is likely to become good.

The content of the aromatic aldehyde having a branched alkyl group having 10 carbon atoms is more preferably 10 to 13% by mass. The content of the aromatic aldehyde having a branched alkyl group having 11 carbon atoms is more preferably 24 to 30% by mass. The content of the aromatic aldehyde having a branched alkyl group having 12 carbon atoms is more preferably 27 to 33% by mass. The content of the aromatic aldehyde having a branched alkyl group having 13 carbon atoms is more preferably 22 to 27% by mass.

Aromatic aldehydes are broadly used also for applications to polyurethane-based sealants. Aromatic aldehydes used for such applications are required not to smell at normal pressure, that is, required to have a boiling point at normal pressure of exceeding 330° C., from the viewpoint of the discharge regulation of volatile organic compounds (VOC), and also required to be a liquid at normal temperature from the viewpoint of the workability. However, usual aromatic aldehydes are known to have a low boiling point, and if the boiling point is attempted to be raised by substitution with a long-chain alkyl group, the melting point also results in rising simultaneously. An example of an aromatic aldehyde substituted with a long-chain alkyl group is 4-(n-nonyl) benzaldehyde, which is obtained by substitution with a straight-chain alkyl group having 9 carbon atoms, and is known to have a melting point of −5° C. and be a liquid at normal temperature (see U.S. Pat. No. 5,371,284, and Helvetica Chimica Acta, (1982), Vol. 65, Issue 8, p. 2448-2449). However, since it has a boiling point of 136 to 139° C./0.55 mmHg and a boiling point at normal pressure of 330° C. or lower, the smelling problem occurs. Further, 4-(n-decyl) benzaldehyde, which is substitution with a straight-chain alkyl group having 10 carbon atoms, has a boiling point of 152 to 156° C./0.3 mmHg and a boiling point at normal pressure of exceeding 330° C., but it has a melting point of 8° C. and may solidify in the wintertime (see U.S. Pat. No. 5,371,284, and Helvetica Chimica Acta, (1982), Vol. 65, Issue 8, p. 2448-2449). Further, p-n-dodecylbenzaldehyde, which is obtained by substitution with a straight-chain alkyl group having 12 carbon atoms, has a melting point of 92° C., and is a solid at normal temperature (see Seishi Shin'ya, "Journal of Agricultural Chemical Society of Japan", 1959, vol. 33, No. 5, p. 362-365).

Since the aromatic aldehyde in the present embodiment is required to be a liquid at normal temperature from the viewpoint of the workability, the temperature at which the aromatic aldehyde solidifies when being cooled (hereinafter, also referred to as "solidifying point") is preferably 0° C. or lower, more preferably −10° C. or lower, and still more preferably −50° C. or lower. The aromatic aldehyde in the present embodiment has such an advantage that the temperature range in a liquid state is wide.

Since an aromatic aldehyde in the present embodiment is required not to smell at normal pressure from the viewpoint of the discharge regulation of volatile organic compounds (VOC), a temperature point at which the aromatic aldehyde vaporizes from a liquid state when being heated at normal pressure (1 atm) (hereinafter, also referred to as "vaporizing point") is preferably higher than 330° C., more preferably 340° C. or higher, and still more preferably 350° C. or higher. The aromatic aldehyde in the present embodiment has a high vaporizing point, and has such an advantage that the aromatic aldehyde can be used as a solvent even at high temperatures.

[Method for Producing the Aromatic Aldehyde]

A method for producing the aromatic aldehyde in the present embodiment is not especially limited, but the aromatic aldehyde can be produced, for example, by a method comprising a step of formylating an aromatic compound which has a branched alkyl group having 10 to 14 carbon atoms with carbon monoxide in the presence of hydrogen fluoride and boron trifluoride.

An aromatic compound which has a branched alkyl group having 10 to 14 carbon atoms (hereinafter, also referred to as "raw material compound") as a raw material may be a mixture of two or more aromatic compounds which have branched alkyl groups having different numbers in 10 to 14 of carbon atoms, and may be a mixture of two or more structural isomers of any one of aromatic compounds each having a branched alkyl group having 10 to 14 carbon atoms.

A method for preparing the raw material compound is not especially limited, and the raw material compound can be prepared, for example, by alkylating one of benzenes with corresponding olefin using an acid catalyst. The raw material compound can be obtained also by separating from tar fractions and petroleum fractions. Commercially available products can also be used, and for example, "Alkene L" (product name, made by JX Nippon Oil & Energy Corp.) may be used as it is. Here, as described in Examples described later, Alkene L contains as a main component a mixture of alkylbenzenes which have branched alkyl groups having 10 to 13 carbon atoms, and contains almost no alkylbenzenes which have straight chain alkyl groups having 10 to 13 carbon atoms.

The formylation reaction of an aromatic compound which has a branched alkyl group having 10 to 14 carbon atoms is preferably carried out by reacting a raw material compound with carbon monoxide in the presence of catalysts of hydrogen fluoride (hereinafter, also referred to as "HF") and boron trifluoride (hereinafter, also referred to as "$BF_3$"). This production method enables to provide an aromatic aldehyde in a good yield and in a purity of 80% or higher. HF and $BF_3$ used as catalysts can be recovered and reutilized, since they have high volatility. That is, used catalysts do not need to be discarded, which is very excellent economically and simultaneously reduced in the environmental load.

Carbon monoxide used in the formylation reaction is allowed to contain inert gases such as nitrogen and methane, but the carbon monoxide partial pressure is preferably 0.5 to 5 MPa, and more preferably 1 to 3 MPa. In the case where the carbon monoxide partial pressure is too low, the formylation reaction does not sufficiently progress and side-reactions such as isomerization and polymerization concurrently occur to reduce the yield; the case is therefore not preferable. Even if the carbon monoxide partial pressure is made to be higher than the above range, no merit can be obtained on the reaction, and the inconvenience including needing a high-pressure apparatus is likely to be brought about.

HF is preferably a substantially anhydrous HF. The amount of HF in the raw material compound is, from the viewpoint of the reaction efficiency, preferably in the range of 8 mol or more and 30 mol or less, and more preferably 15 mol or more and 25 mol or less, with respect to 1 mol of the raw material compound.

The amount of $BF_3$ in the raw material compound is, from the viewpoint of the reaction efficiency, preferably in the range of 1.5 mol or more and 3.5 mol or less, and more preferably 2.0 mol or more and 3.0 mol or less, with respect to 1 mol of the raw material compound.

The reaction temperature in the formylation reaction is, from the viewpoint of suppressing by-production of polymerization products to improve the yield, preferably in the range of −45° C. or higher and −15° C. or lower, more preferably −40° C. or higher and −20° C. or lower, and still more preferably −35° C. or higher and −25° C. or lower. The reaction time is, from the viewpoint of improving the conversion rate of the raw material compound, preferably 1 to 5 hours.

From the viewpoint of the solubility of the raw material compound, as a solvent, a reaction solvent inert to the raw material compound and HF/$BF_3$, for example, a saturated aliphatic hydrocarbon such as hexane, heptane or decane, may be used. In this case, the polymerization reaction is further suppressed and the yield is improved; however, since use of a large amount of a solvent reduces the volume efficiency of the reaction, and brings about the increase of the unit energy requirement needed for the separation, the presence/absence and the use amount of a solvent are suitably determined.

A reaction mode of the formylation reaction is not especially limited as long as involving a stirring method capable of sufficiently mixing a liquid phase and a gas phase, and any type of a batch type, a semi-batch type, a continuous type and the like can be employed.

An example of the batch type is as follows: a raw material compound dissolved in a solvent, anhydrous HF and $BF_3$ are placed in an autoclave equipped with an electromagnetic stirring apparatus; the content is stirred and the liquid temperature is held at −45° C. or higher and −15° C. or lower; then, the pressure is raised to 0.5 to 5 MPa by carbon monoxide; thereafter, while keeping the pressure and the liquid temperature, the content is held for 1 to 5 hours till the carbon monoxide comes not to be absorbed; and then, the reaction product liquid is poured in ice.

An example of the semi-batch type is as follows: anhydrous HF and $BF_3$ are placed in an autoclave equipped with an electromagnetic stirring apparatus; the content is stirred, and the liquid temperature is set at −45° C. or higher and −15° C. or lower and held constant; then, the pressure is raised to 0.5 to 5 MPa by carbon monoxide, and carbon monoxide is fed while holding the pressure constant; thereafter, a raw material compound dissolved in a solvent is fed; and, after the state is held for 0.1 to 3 hours, the reaction product liquid is poured in ice.

An example of the continuous type is as follows: anhydrous HF and $BF_3$ are placed in an autoclave equipped with an electromagnetic stirring apparatus; the content is stirred, and the liquid temperature is set at −45° C. or higher and −15° C. or lower and held constant; then, the pressure is raised to 0.5 to 5 MPa by carbon monoxide, and carbon monoxide is fed while holding the pressure constant; thereafter, a raw material compound dissolved in a solvent is fed to carry out the reaction of the semi-batch type; and successively, feed of anhydrous HF and $BF_3$ is started, and the reaction product liquid is continuously drawn out into ice water. The time period during which the reaction liquid stays in the autoclave is preferably 1 to 5 hours from the viewpoint of the reaction efficiency. The reaction end point is not especially limited, but for example, the reaction can be ended when the absorption of carbon monoxide stops.

In the above formylation reaction, since the reaction product liquid poured in ice or ice water contains a trace amount of HF in some cases, the reaction product liquid is preferably subjected to a water washing for neutralization using a 0.5% sodium hydroxide aqueous solution. By analyzing an oil layer obtained by the neutralization by gas chromatography, the formation of an aromatic aldehyde can be confirmed. Thereafter, by refining the oil layer by a usual refining method suitably selected such as distillation operation and liquid chromatography, a target aromatic aldehyde can be obtained.

[Epoxy Resin Curing Agent]

The epoxy resin curing agent in the present embodiment comprises (A) a polyamine compound and (B) the above aromatic aldehyde which has a branched alkyl group having 10 to 14 carbon atoms.

((A) Polyamine Compound)

The polyamine compound in the present embodiment is not especially limited, but is preferably one or more selected from the group consisting of polyamines represented by the following general formula (A1), linear aliphatic polyamines represented by the following general formula (A2) and compounds obtained by adding a polyamine represented by the following general formula (A1) or (A2) to a compound having at least one glycidyl group in one molecule thereof.

$$H_2N-CH_2-A-CH_2-NH_2 \quad (A1)$$

wherein A represents a phenylene group or a cyclohexylene group.

$$H_2N-(CH_2CH_2NH)_n-CH_2CH_2NH_2 \quad (A2)$$

wherein n represents an integer of 0 to 4.

The polyamine compounds represented by the above general formula (A1) include orthoxylylenediamine, metaxylylenediamine, paraxylylenediamine, 1,2-bis(aminomethyl)cyclohexane, 1,3-bis(aminomethyl)cyclohexane and 1,4-bis(aminomethyl)cyclohexane. Among these, metaxylylenediamine and 1,3-bis(aminomethyl)cyclohexane are preferable from the viewpoint of mechanical properties, and chemical resistance of a cured material, and the like.

The linear aliphatic polyamines represented by the above general formula (A2) include ethylenediamine, diethylenetriamine, triethylenetetramine, tetraethylenepentamine and pentaethylenehexamine. Among these, diethylenetriamine and triethylenetetramine are preferable from the viewpoint of the reactivity, the mechanical properties and the like.

The compounds having at least one glycidyl group in one molecule thereof (hereinafter, also referred to as "epoxy resin") include butyl glycidyl ether, phenyl glycidyl ether, metacresyl glycidyl ether, paracresyl glycidyl ether, orthocresyl glycidyl ether, neodecanoic acid glycidyl ester, 4,4'-isopropylidenediphenol diglycidyl ether (bisphenol A-based epoxy resin), 4,4'-methylenediphenol diglycidyl ether (bisphenol F-based epoxy resin), neopentylglycol diglycidyl ether, 1,2-propanediol diglycidyl ether, 1,4-butanediol diglycidyl ether and 1,6-hexanediol diglycidyl ether. Among these, the bisphenol A-based epoxy resin and the bisphenol F-based epoxy resin are preferable from the viewpoint of the mechanical properties, and the chemical resistance of a cured material, and the like.

As a method of adding a polyamine compound to an epoxy resin, a conventionally well-known method can be used. An example thereof is as follows: a polyamine compound is placed in a reaction apparatus in an excessive amount to an epoxy equivalent of an epoxy resin; and then, the epoxy resin is dropwise added thereto, and heated to allow to react.

((B) Aromatic Aldehyde)

The aromatic aldehyde in the present embodiment is the above-mentioned aromatic aldehyde which has a branched alkyl group having 10 to 14, preferably 10 to 13 carbon atoms, and may be a mixture thereof. Incorporation of the above-mentioned aromatic aldehyde which has a branched alkyl group having 10 to 14 carbon atoms in an epoxy resin curing agent enables to improve the surface property, drying property, water resistance, transparency and adhesion of epoxy resin coating films and epoxy resin cured materials obtained by using the curing agent.

(Epoxy Resin Curing Agent)

The epoxy resin curing agent in the present embodiment comprises (A) the above polyamine compound and (B) the above aromatic aldehyde. The epoxy resin curing agent may comprise optional other components, as long as the advantage of the present invention is not impaired.

The epoxy resin curing agent in the present embodiment may be either of one-pack type and two-pack type. The one-pack type curing agent can be obtained by mixing (A) the above polyamine compound and (B) the above aromatic aldehyde. The mixing can be carried out by using a conventionally well-known apparatus, and examples of the apparatuses include a dissolver, a high-speed mixer, a homomixer, a kneader and a roll mill.

The two-pack type curing agent is used by mixing (A) a polyamine compound and (B) an aromatic aldehyde when being applied to an epoxy resin. (A) The polyamine compound and (B) the aromatic aldehyde forms a Schiff base when being mixed, and at this time, deposits are formed along with the formation of the Schiff base in some cases. In the case where the deposits are formed, since the appearance of a cured material is likely to be deteriorated, the epoxy resin curing agent is preferably a two-pack type curing agent. The content of the aromatic aldehyde is preferably determined suitably in the range of not forming deposits.

[Epoxy Resin Composition]

The epoxy resin composition in the present embodiment comprises an epoxy resin and the above epoxy resin curing agent. The epoxy resin to be used for the epoxy resin composition in the present embodiment is not especially limited as long as being an epoxy resin having a glycidyl group reactive with an active hydrogen originated from an amino group contained in the epoxy resin curing agent, but an epoxy resin is suitably used which comprises as a main component a bisphenol A-based epoxy resin, a bisphenol F-based epoxy resin or a mixture thereof from the viewpoint of the mechanical properties and the chemical resistance of a cured material, and the like.

The epoxy resin composition in the present embodiment may further comprise, depending on applications, modifying components such as a filler and a plasticizer; flow regulating components such as a reactive or non-reactive diluent and a thixotropy imparting material; and components such as a pigment and a tackifier, and additives such as an anti-repelling agent, a flowing agent, a defoaming agent, an ultraviolet absorbent, a light stabilizer and a curing accelerator, as long as the advantage of the present invention is not impaired.

The epoxy resin composition in the present embodiment is especially suitable for coating applications and civil engineering and construction applications. The epoxy resin composition in the present embodiment can be cured by a known method to form an epoxy resin cured material such as a cured coating film. The curing condition can suitably be selected depending on applications, as long as the advantage of the present invention is impaired.

EXAMPLES

Hereinafter, the present invention will be described specifically by way of Examples. However, the present invention is not limited to these Examples at all.

[Analysis Instruments]

(1) Gas Chromatography

A gas chromatograph "GC-17A" (trade name, made by Shimadzu Corp.) and a capillary column "HR-1" (trade name, made by Shinwa Chemical Industries Ltd., 0.32 mmϕ×25 m)

Temperature-rise condition: the temperature was raised from 100° C. to 320° C. at 5° C./min.

(2) Liquid Chromatography

A recycle preparative HPLC apparatus "LC-9110NEXT" (trade name, made by Japan Analytical Industry Co., Ltd.)

(3) A GC-MS Apparatus

A GC-MS spectrum apparatus "POLARIS Q" (trade name, made by Thermo Electron Corp.)

(4) An NMR apparatus 1

"Avance II (600 MHz-NMR)" (trade name, made by Bruker Biospin GmbH)

Mode: Proton, Carbon, dept135, HSQC, HMBC, H2BC

Solvent: $CDCl_3$ (deuterated chloroform)

Internal standard substance: tetramethylsilane (5) An NMR Apparatus 2

"JNM-AL400 type (400 MHz)" (trade name, made by JEOL Ltd.)

Solvent: $CDCl_3$ (deuterated chloroform)

Internal standard substance: tetramethylsilane

[Evaluation of the Performance of an Epoxy Resin Coating Film]

An epoxy resin composition was coated in a thickness of 200 μm on a steel plate under the condition of 23° C. and 50% RH.

<Appearance (Gloss, Transparency, Smoothness)>

The coating film appearance (gloss, transparency, smoothness) after 7 days of curing was visually evaluated. The appearance was evaluated based on the following 5 grades, and grades of 3 or more were determined to be practicable.

(Gloss)
  5: excellent (light was reflected in the coating film)
  4: good (light was nearly reflected in the coating film)
  3: fair (portions exposed to light could be recognized but the reflection was little)
  2: slightly poor (portions exposed to light could hardly be confirmed)
  1: poor (portions exposed to light could not be recognized)
(Transparency)
  5: excellent (the coated plate surface was easily confirmed)
  4: good (the coated plate surface could nearly be confirmed)
  3: fair (the coated plate surface could barely be confirmed)
  2: slightly poor (the coating film was slightly cloudy, and the coated plate surface could hardly be confirmed)
  1: poor (the coating film was cloudy, and the coated plate surface could not be observed)
(Smoothness)
  5: excellent (images were reflected in the coating film like a mirror surface)
  4: good (some portions of images reflected in the coating film were slightly disturbed)
  3: fair (images reflected in the coating film were slightly disturbed, but recognizable)
  2: slightly poor (images were reflected in the coating film, but unrecognizable)
  1: poor (no image was reflected in the coating film)
<Dry-to-Touch Property>
  Coating films after 16 hours, and 1, 4 and 7 days of curing were evaluated by finger touch. The dry-to-touch property was evaluated based on the following 5 grades, and grades of 3 or more were determined to be practicable.
  5: excellent (no tackiness of the coating film was observed even in a long-time (about 1 min) touch, and no remaining of fingerprints was observed after the touch)
  4: good (no tackiness of the coating film was observed at the time of touch, and no remaining of fingerprints was observed after the touch)
  3: fair (no tackiness of the coating film surface was observed, but fingerprints remained after the touch)
  2: slightly poor (tackiness of the coating film surface was observed, and fingerprints remained after the touch)
  1: poor (uncured)
<Water Resistance>
  Water droplets were dropped on coating films after 16 hours, and 1, 4 and 7 days of curing; and changes in the coating films after being left for 1 day were visually evaluated. The water resistance was evaluated based on the following 5 grades, and grades of 3 or more were determined to be practicable.
  5: excellent (no difference from no water droplet-dropped portions was observed)
  4: good (no change in the surface state (gloss) of the coating film was observed, but dropped portions could be discriminated depending on the light ray condition)
  3: fair (no change in the surface state (gloss) of the coating film was observed, but whitening was confirmed depending on the light ray condition)
  2: slightly poor (the surface state (gloss) of the coating film was slightly reduced, and water droplet-dropped portions could distinctly be discriminated)
  1: poor (whitening and/or depressions occurred on water droplet-dropped portions)

<Adhesion to a Base Material>
  Grid-like scores having the number of cells of 25 with gap intervals of 2 mm were scribed on the coating film after 7 days of curing; a pressure-sensitive adhesive tape was pasted on the grid-like scores and peeled off, and the adhesion was evaluated based on the remaining number of the cells of the coating film. The operation of the pasting and the peeling-off of the pressure-sensitive adhesive tape were carried out two times.

Production Example 1

Preparation of a Branched Dodecylbenzene Mixture

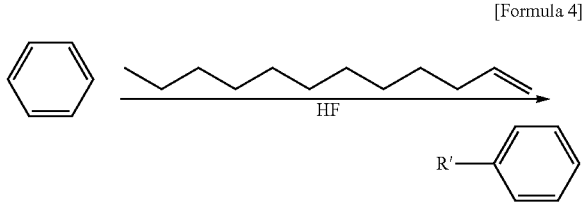

[Formula 4]

(In the formula, R' represents a branched alkyl group having 12 carbon atoms.)

In a temperature-controllable 500 mL-internal volume autoclave (its material: SUS316L) equipped with an electromagnetic stirring apparatus, 59.5 g (2.97 mol) of anhydrous hydrogen fluoride and 139.4 g (1.78 mol) of benzene were charged, and the content was stirred; and 100.1 g (0.59 mol) of n-dodecene (made by Tokyo Chemical Industry Co., Ltd.) was fed with the liquid temperature being held at 45° C., and the resulting system was held for 1 hour. Thereafter, the reaction product was poured in ice and subjected to a neutralization treatment.

When the obtained oil layer was analyzed by gas chromatography, the conversion rate of n-dodecene was 100% by mass, and the yield of a branched dodecylbenzene mixture was 98.4% by mass (in terms of n-dodecene).

The reaction liquid was refined by a 20-stage distillation column to thereby obtain 116.4 g of the branched dodecylbenzene mixture.

Example 1

(Production of a Branched Dodecylbenzaldehyde by Formylation of the Branched Dodecylbenzene Mixture)

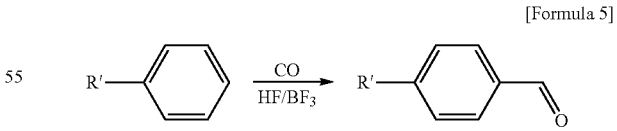

[Formula 5]

(In the formula, R' represents a branched alkyl group having 12 carbon atoms.)

In a temperature-controllable 500 mL-internal volume autoclave (its material: SUS316L) equipped with an electromagnetic stirring apparatus, 92.6 g (4.63 mol) of anhydrous hydrogen fluoride and 39.2 g (0.58 mol) of boron trifluoride were charged, and the content was stirred; and the pressure was raised to 2 MPa by carbon monoxide with the liquid temperature being held at −30° C. Thereafter, 57.0 g (0.23 mol) of the branched dodecylbenzene mixture prepared in Production Example 1 was fed with the pressure being held at 2 MPa and the liquid temperature being held at −30° C., and the resulting system was held for 1 hour; thereafter, the content was poured in ice, diluted with n-heptane, and subjected to a neutralization treatment; and an oil layer obtained thereby was analyzed by gas chromatography to determine a reaction result. Then, the conversion rate of the branched dodecylbenzene mixture was 100%, and the yield of the total of branched dodecylbenzaldehydes was 84.9% by mass (in terms of dodecylbenzene). The yield of 4-(dodecan-6-yl)benzaldehyde and 4-(dodecan-5-yl)benzaldehyde as main products to be identified in the below was 34.4% by mass (in terms of the branched dodecylbenzene mixture as the raw material).

The obtained liquid was subjected to a simple distillation to thereby obtain as a main fraction (182 to 190° C./6 torr) 43.0 g of the total of 4-(dodecan-6-yl)benzaldehyde and 4-(dodecan-5-yl)benzaldehyde to be identified in the below (the total yield of both the aldehydes was 67.7% by mol; in terms of the branched dodecylbenzene mixture as the raw material). The branched dodecylbenzaldehyde mixture had a vaporizing point at normal pressure of 350° C. The main fraction had little aldehyde odor, and exhibited as low a value of a solidifying point as −66° C.

(Identification of the Product)

The main products were further rectified using a rectifying column having the number of theoretical plates of 50, and thereafter subjected to liquid chromatography to thereby fractionally collect two components (Components 1 and 2). The molecular weights of the two components were measured by GC-MS, and were both 274.

The each component was subjected to, by using the above NMR apparatus 1, a $^1$H-NMR measurement, a $^{13}$C-NMR measurement, a dept135-NMR measurement, an HSQC-NMR measurement, an H2BC-NMR measurement, and an HMBC-NMR measurement. The results of the $^1$H-NMR measurement and the $^{13}$C-NMR measurement are shown in the below, and the results of the dept135-NMR measurement, the HSQC-NMR measurement, the H2BC-NMR measurement and the HMBC-NMR measurement are shown in FIGS. 1 to 12.

<The Result of the NMR Measurement of 4-(Dodecan-6-yl)benzaldehyde>

$^1$H-NMR (600 MHz, CDCl$_3$, TMS, ppm) δ: 0.81-0.85 (t, 6H), 1.07-1.23 (m, 14H), 1.55-1.65 (m, 4H), 2.58 (m, 1H), 7.30 (d, 2H), 7.80 (d, 2H), 9.98 (s, 1H)

$^{13}$C-NMR (600 MHz, CDCl$_3$, TMS, ppm) δ: 14.039, 14.060, 22.512, 22.604, 27.230, 27.530, 29.337, 31.715, 31.868, 36.680, 36.731, 46.452, 128.348, 129.880, 134.571, 154.233, 192.113

<The Result of the NMR Measurement of 4-(Dodecan-5-yl)benzaldehyde>

$^1$H-NMR (600 MHz, CDCl$_3$, TMS, ppm) δ: 0.81-0.86 (t, 6H), 1.06-1.25 (m, 14H), 1.57-1.65 (m, 4H), 2.57 (m, 1H), 7.30 (d, 2H), 7.80 (d, 2H), 9.98 (s, 1H)

$^{13}$C-NMR (600 MHz, CDCl$_3$, TMS, ppm) δ: 13.983, 14.082, 22.625, 22.722, 27.576, 29.168, 29.633, 29.781, 31.813, 36.432, 36.728, 46.441, 128.352, 129.881, 134.574, 154.234, 192.110

FIG. 1 shows a result of the dept135-NMR measurement on Component 1. It is clear from FIG. 1 that 12 types of alkyl carbon atoms were present; two primary carbon atoms were present; 9 secondary carbon atoms were present; and 1 tertiary carbon atom was present.

FIG. 2 shows a result of the HSQC-NMR measurement on Component 1. Hydrogen atoms bonded to each carbon atom can be grasped from FIG. 2.

FIG. 3 shows a result of the H2BC-NMR measurement on Component 1. FIG. 3 indicates a correlation only of two bonds of C—H.

FIG. 4 is an enlarged view of the part from 0.2 to 2.7 ppm of the measurement result (the part surrounded by a dotted line in FIG. 3, and relevant to an alkyl group) in FIG. 3. There can be distinguished from FIG. 4 adjacent situations of carbon atoms indicated by white circle symbols, a black circle symbol, white square symbols, black square symbols and black triangle symbols. Three carbon atoms indicated by the mark "x" could not be identified because the $^1$H-NMR measurement peaks each and the $^{13}$C-NMR measurement peaks each were near.

FIG. 5 shows a result acquired by studying isomer candidate compounds by using the measurement result of FIG. 4. Since no correlation signal which should be detected if assumption was made that Component 1 was 4-(dodecan-2-yl)benzaldehyde, 4-(dodecan-3-yl)benzaldehyde or 4-(dodecan-4-yl)benzaldehyde was detected, it is clear that Component 1 was not 4-(dodecan-2-yl)benzaldehyde, 4-(dodecan-3-yl)benzaldehyde or 4-(dodecan-4-yl)benzaldehyde.

FIG. 6 shows a result of the HMBC-NMR measurement on Component 1. In FIG. 6, since no correlation signal was detected on HMBC, it is clear that hydrogen atoms bonded to carbon indicated by white square symbols were 4 or more bonds away from carbon atoms indicated by black square symbols.

FIG. 7 shows a result of the dept135-NMR measurement on Component 2. It is clear from FIG. 7 that 12 types of alkyl carbon atoms were present; two primary carbon atoms were present; 9 secondary carbon atoms were present; and 1 tertiary carbon atom was present.

FIG. 8 shows a result of the HSQC-NMR measurement on Component 2. Hydrogen atoms bonded to each carbon atom can be grasped from FIG. 8.

FIG. 9 shows a result of the H2BC-NMR measurement on Component 2. FIG. 9 indicates a correlation only of two bonds of C—H.

FIG. 10 is an enlarged view of the part from 0.2 to 2.9 ppm of the measurement result (the part surrounded by a dotted line in FIG. 9, and relevant to an alkyl group) in FIG. 9. There can be distinguished from FIG. 10 adjacent situations of carbon atoms indicated by white circle symbols, a black circle symbol, white square symbols, black square symbols and black triangle symbols. Three carbon atoms indicated by the mark "x" could not be identified because the $^1$H-NMR measurement peaks each and the $^{13}$C-NMR measurement peaks each were near.

FIG. 11 shows a result acquired by studying isomer candidate compounds by using the measurement result of FIG. 10. Since correlation signals which should be detected on the assumption that Component 2 was 4-(dodecan-2-yl)benzaldehyde, 4-(dodecan-3-yl)benzaldehyde or 4-(dodecan-4-yl)benzaldehyde were not detected, it is clear that Component 2 was not 4-(dodecan-2-yl)benzaldehyde, 4-(dodecan-3-yl)benzaldehyde or 4-(dodecan-4-yl)benzaldehyde.

FIG. 12 shows a result of the HMBC-NMR measurement on Component 2. It is clear from FIG. 12 that since correlation signals were detected between hydrogen atoms bonded to carbon indicated by white square symbols and carbon atoms indicated by black square symbols, these were present within 3 or less bonds.

Comprehensively judging from these measurement results, Component 1 was identified to be 4-(dodecan-6-yl)benzaldehyde, and Component 2 was identified to be 4-(dodecan-5-yl)benzaldehyde.

Example 2

(Production of an Alkylbenzaldehyde Mixture)

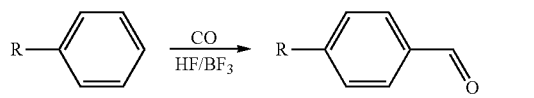

[Formula 6]

(In the formula, R represents a branched alkyl group having 10 to 13 carbon atoms.)

"Alkene L" (product name, made by JX Nippon Oil & Energy Corp., average molecular weight: 241) was used as a raw material. The molecular weight of Alkene L was analyzed by GC-MS, and was identified to contain a mixture of benzenes substituted with an alkyl group having 10 to 13 carbon atoms as a main component. Authentic samples of n-decylbenzene ($C_{16}H_{26}$), n-undecylbenzene ($C_{17}H_{28}$), n-dodecylbenzene ($C_{18}H_{30}$) and n-tridecylbenzene ($C_{19}H_{32}$) were over-injected and the contents of the respective straight chain alkyl group-substituted benzenes in Alkene L were identified to be 0%, 0.28%, 0% and 0.09%. From this result, Alkene L was identified to be a mixture of benzenes substituted with a branched alkyl group having 10 to 13 carbon atoms.

In a temperature-controllable 500 mL-internal volume autoclave (its material: SUS316L) equipped with an electromagnetic stirring apparatus, 82.6 g (4.13 mol) of anhydrous hydrogen fluoride and 35.0 g (0.52 mol) of boron trifluoride were charged, and the content was stirred; and the pressure was raised to 2 MPa by carbon monoxide with the liquid temperature being held at −30° C. Thereafter, 49.7 g (0.21 mol) of Alkene L was fed with the pressure being held at 2 MPa and the liquid temperature being held at −30° C., and the resulting system was held for 1 hour; thereafter, the content was poured in ice, diluted with n-heptane, and thereafter subjected to a neutralization treatment; and an oil layer obtained thereby was analyzed by gas chromatography to determine a reaction result. Then, the conversion rate of the alkylbenzene having a branched alkyl group having 10 to 13 carbon atoms was 100% by mass; the yield of a para-substituted benzaldehyde having a branched alkyl group having 10 carbon atoms was 10.6% by mass; the yield of a para-substituted benzaldehyde having a branched alkyl group having 11 carbon atoms was 24.7% by mass; the yield of a para-substituted benzaldehyde having a branched alkyl group having 12 carbon atoms was 27.7% by mass; the yield of a para-substituted benzaldehyde having a branched alkyl group having 13 carbon atoms was 22.2% by mass; and the yield of the total of the para-substituted benzaldehydes having a branched alkyl group having 10 to 13 carbon atoms was 85.2% by mass (in terms of Alkene L).

Among the above, the total yield of 4-(dodecan-6-yl)benzaldehyde and 4-(dodecan-5-yl)benzaldehyde was 10.4% by mass (in terms of Alkene L).

The obtained liquid was subjected to a simple distillation to thereby obtain as a main fraction (187 to 230° C./8 torr) 40.9 g (isolated yield: 73.6% by mol, in terms of Alkene L) of the benzaldehydes in which the yield of a para-substituted benzaldehyde having a branched alkyl group having 10 carbon atoms was 11.0% by mass; the yield of a para-substituted benzaldehyde having a branched alkyl group having 11 carbon atoms was 27.3% by mass; the yield of a para-substituted benzaldehyde having a branched alkyl group having 12 carbon atoms was 31.4% by mass; and the yield of a para-substituted benzaldehyde having a branched alkyl group having 13 carbon atoms was 25.0% by mass. Among these, the total content of 4-(dodecan-6-yl)benzaldehyde and 4-(dodecan-5-yl)benzaldehyde was 10.4% by mass (4.3 g, 3.2% by mol, in terms of Alkene L). No variation in the composition ratio due to the distillation was observed.

As a result of analysis of the main fraction by GC-MS, molecular weights of 246, 260, 274 and 288 were detected. The product was subjected to a $^1$H-NMR measurement using the NMR apparatus 2. The $^1$H-NMR measurement results are shown in the below.

$^1$H-NMR (400 MHz, CDCl$_3$, TMS, ppm) δ: 0.86 (m, 6H), 1.65 (m, 14H), 1.55 (m, 4H), 2.58 (m, 1H), 7.30 (d, 2H), 7.80 (d, 2H), 9.97 (s, 1H)

In consideration of the GC-MS measurement results and the molecular weight of the raw material, the product was identified to be a mixture of benzaldehydes having an alkyl group having 10, 11, 12 or 13 carbon atoms. Further from the $^1$H-NMR measurement results, although the structures of single compounds of the product could not be specified, it was specified that the number of CH$_3$ terminals was 2 from the peak of 0.86 (m, 6H). In collective consideration of these measurement results, the product was presumed to be a mixture of benzaldehydes having a branched alkyl group having 10, 11, 12 or 13 carbon atoms. The main fraction had little aldehyde odor, and exhibited as low a value of a melting point as −65° C.

Comparative Example 1

(Production of 4-n-undecylbenzaldehyde)

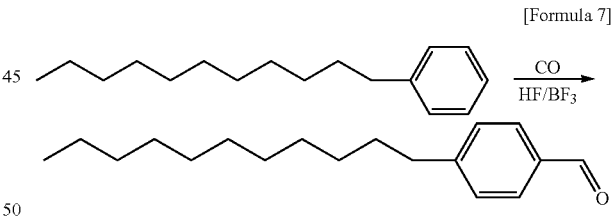

[Formula 7]

The formylation reaction and the treatment of a reaction product liquid were carried out as in Example 2, except for using 48.0 g (0.21 mol) of n-undecylbenzene (made by Tokyo Chemical Industry Co., Ltd.) in place of Alkene L as a raw material. An obtained oil layer was analyzed by gas chromatography to thereby determine a reaction result; then, the conversion rate of n-undecylbenzene was 99.7% by mass, and the selection rate of 4-n-undecylbenzaldehyde was 98.4% by mass (in terms of n-undecylbenzene). An obtained liquid was subjected to a simple distillation to thereby obtain 45.0 g (isolated yield: 83.7% by mass, in terms of n-undecylbenzene) of 4-n-undecylbenzaldehyde of 98.8% by mass as a main fraction (197 to 210° C./7 torr). Since the melting point of the fraction was measured, and was 14° C., 4-n-undecylbenzaldehyde was revealed not to be a liquid at normal temperature. Further since the fraction has little aldehyde odor at normal pressure, the fraction was presumed to have a high boiling point.

Production Example 2

(Polyamine Compound A)

In a 2 L-internal volume separable flask equipped with a stirrer, a thermometer, a nitrogen introducing tube, a dropping funnel and a cooling tube, 1,066.8 g (7.5 mol) of 1,3-bis(aminomethyl)cyclohexane (made by Mitsubishi Gas Chemical Company, Inc.; hereinafter, referred to as "1,3-BAC") was charged, and heated to 80° C. in a nitrogen flow under stirring. 558 g of a bisphenol A-based epoxy resin (made by Mitsubishi Chemical Corp.; product name: JER828, epoxy equivalent: 186 g/eq; hereinafter, referred to as "DGEBA") was dropwise added thereto over 2 hours with the temperature being held at 80° C. After the finish of the dropping, the temperature was raised to 100° C. and the reaction was carried out for 2 hours to thereby obtain 1,615.5 g of a DGEBA adduct of 1,3-BAC (polyamine compound A).

Production Example 3

(Polyamine Compound B)

Except for using 1,021.5 g (7.5 mol) of metaxylylenediamine (made by Mitsubishi Gas Chemical Company, Inc.; hereinafter referred to as "MXDA") in place of 1,3-BAC, 1,561.3 g of a DGEBA adduct of MXDA (polyamine compound B) was obtained as in Production Example 2.

Production Example 4

(Polyamine Compound C)

Except for using 773.8 g (7.5 mol) of diethylenetriamine (made by Kanto Chemical Co., Inc.; hereinafter referred to as "DETA") in place of 1,3-BAC, 1,320.0 g of a DGEBA adduct of DETA (polyamine compound C) was obtained as in Production Example 2.

Production Example 5

(Polyamine Compound D)

Except for using 1,096.7 g (7.5 mol) of triethylenetetramine (made by Kanto Chemical Co., Inc.; hereinafter referred to as "TETA") in place of 1,3-BAC, 1,641.7 g of a DGEBA adduct of TETA (polyamine compound D) was obtained as in Production Example 2.

Example 3

In a 145-mL glass-made mayonnaise jar, 85.5 g of polyamine compound A obtained in Production Example 2 was weighed, and 9.5 g of benzyl alcohol and 5.0 g of the alkylbenzaldehyde mixture obtained in Example 2 were added thereto. The resulting mixture was stirred at 60° C. for 2 min to thereby obtain 100 g of an epoxy resin curing agent A.

The obtained epoxy resin curing agent A was blended with the epoxy resin (DGEBA) to thereby obtain an epoxy resin composition. The blending was carried out in a proportion indicated in Table 1, in which the active hydrogen in the curing agent and the epoxy group in the DGEBA became equimolar. The obtained epoxy resin composition was applied in a thickness of 200 μm on a steel plate under the condition of 23° C./50% RH, and cured to thereby fabricate an epoxy resin cured coating film. The evaluation results are shown in Table 1.

Examples 4 to 6

Except for using polyamine compounds B to D obtained in Production Examples 3 to 5 in place of polyamine compound A, 100 g of the epoxy resin curing agents B to D were obtained as in Example 3, respectively.

Epoxy resin compositions were obtained, and epoxy resin cured coating films were fabricated, as in Example 3, except for using the epoxy resin curing agents B to D in place of the epoxy resin curing agent A. The evaluation results are shown in Table 1.

Comparative Examples 2 to 5

In a 145-mL glass-made mayonnaise jar, 90.0 g of polyamine compounds A to D obtained in Production Examples 2 to 5 were weighed, and 10.0 g of benzyl alcohol was added thereto. The resulting mixture was stirred at 60° C. for 2 min to thereby obtain 100 g of epoxy resin curing agents E to H, respectively.

Epoxy resin compositions were obtained, and epoxy resin cured coating films were fabricated, as in Example 3, except for using the epoxy resin curing agents E to H in place of the epoxy resin curing agent A. The evaluation results are shown in Table 2.

TABLE 1

| | Example 3 | Example 4 | Example 5 | Example 6 |
|---|---|---|---|---|
| Epoxy Resin Composition | | | | |
| epoxy resin (g) | 100 | 100 | 100 | 100 |
| epoxy resin curing agent A (g) | 37 | | | |
| epoxy resin curing agent B (g) | | 38 | | |
| epoxy resin curing agent C (g) | | | 31 | |
| epoxy resin curing agent D (g) | | | | 39 |
| Performance of Cured Coating Film | | | | |
| Appearance | | | | |
| Gloss | 4 | 4 | 4 | 4 |
| Transparency | 4 | 4 | 3 | 3 |
| Smoothness | 4 | 4 | 4 | 4 |
| Dry-To-Touch Property (16 hours/1/4/7 days) | 4/4/4/4 | 4/4/4/4 | 4/4/4/4 | 4/4/4/4 |
| Water Resistance (16 hours/1/4/7 days) | 2/2/3/4 | 2/2/3/4 | 2/2/3/4 | 2/2/3/4 |
| Adhesion to Base Material (remaining number of coating film) | 25 | 25 | 25 | 25 |

TABLE 2

| | Comparative Example 2 | Comparative Example 3 | Comparative Example 4 | Comparative Example 5 |
|---|---|---|---|---|
| Epoxy Resin Composition | | | | |
| epoxy resin (g) | 100 | 100 | 100 | 100 |
| epoxy resin curing agent E (g) | 35 | | | |

TABLE 2-continued

| | Comparative Example 2 | Comparative Example 3 | Comparative Example 4 | Comparative Example 5 |
|---|---|---|---|---|
| epoxy resin curing agent F (g) | 36 | | | |
| epoxy resin curing agent G (g) | | 29 | | |
| epoxy resin curing agent H (g) | | | | 37 |
| Performance of Cured Coating Film | | | | |
| Appearance | | | | |
| Gloss | 2 | 2 | 2 | 2 |
| Transparency | 2 | 2 | 1 | 2 |
| Smoothness | 4 | 3 | 4 | 3 |
| Dry-To-Touch Property (16 hours/1/4/7 days) | 3/3/3/3 | 2/2/2/2 | 3/3/3/3 | 3/3/3/3 |
| Water Resistance (16 hours/1/4/7 days) | 1/1/2/2 | 1/1/1/2 | 1/1/2/2 | 1/1/2/2 |
| Adhesion to Base Material (remaining number of coating film) | 25 | 25 | 25 | 25 |

As is clear from the results of Table 1, any of the cured coating films of the epoxy resin compositions using the epoxy resin curing agents of Examples 3 to 6 comprising the aromatic aldehyde according to the present embodiment satisfies all of the excellent surface property (smoothness, gloss), drying property, water resistance, transparency and adhesion, and could be improved in the gloss, transparency, drying property and water resistance as compared with the cured coating films of the epoxy resin compositions using the epoxy resin curing agents of Comparative Examples 2 to 5 comprising no aromatic aldehyde according to the present embodiment.

The present application is based on Japanese Patent Application (Japanese Patent Application No. 2012-121735), filed on May 29, 2012, the entire contents of which are hereby incorporated by reference.

INDUSTRIAL APPLICABILITY

The epoxy resin curing agent and the epoxy resin composition comprising the epoxy resin curing agent according to the present invention, since being able to provide epoxy resin coating films and epoxy resin cured materials satisfying all of the excellent surface property (smoothness, gloss), drying property, water resistance, transparency and adhesion, are useful for coating applications and civil engineering and construction applications. The aromatic aldehyde according to the present invention is useful also as a production raw material for various types of industrial chemical raw materials, pharmaceuticals, agrochemicals, optical functional materials and electronic functional materials.

The invention claimed is:

1. An epoxy resin curing agent, comprising (A) a polyamine compound and (B) an aromatic aldehyde comprising a branched alkyl group,
   wherein the branched alkyl group has 10 to 14 carbon atoms, and wherein the aromatic aldehyde is represented by the following formula (II):

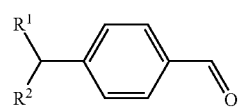

(II)

wherein $R^1$ and $R^2$ each independently represent an alkyl group comprising 1 to 12 carbon atoms, and a total number of the carbon atoms of $R^1$ and $R^2$ is 9 to 13.

2. The epoxy resin curing agent according to claim 1, wherein (A) the polyamine compound is at least one selected from the group consisting of a polyamine represented by the following formula (A1), a linear aliphatic polyamine represented by the following formula (A2), and a compound obtained by adding a polyamine represented by the following formula (A1) or (A2) to a compound comprising a glycidyl group in one molecule thereof:

wherein A is a phenylene group or a cyclohexylene group; and

3. An epoxy resin composition, comprising the epoxy resin curing agent according to claim 1.

4. The epoxy resin composition according to claim 3, for coating or for civil engineering and construction.

5. A cured epoxy resin coating film, manufactured by curing the epoxy resin composition according to claim 3.

6. A cured epoxy resin, manufactured by curing the epoxy resin composition according to claim 3.

7. A method for producing an aromatic aldehyde, wherein the aromatic aldehyde is represented by the following formula (II):

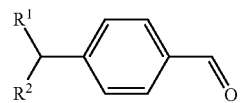

(II)

wherein $R^1$ and $R^2$ each independently represent an alkyl group comprising 1 to 12 carbon atoms, and a total number of the carbon atoms of $R^1$ and $R^2$ is 9 to 13,
   the method comprising formylating an aromatic compound which has a branched alkyl group comprising 10 to 14 carbon atoms with carbon monoxide in the presence of hydrogen fluoride and boron trifluoride.

8. The epoxy resin curing agent according to claim 1, wherein the aromatic aldehyde is at least one selected from the group consisting of 4-(dodecan-6-yl)benzaldehyde and 4-(dodecan-5-yl)benzaldehyde.

* * * * *